United States Patent [19]
Schlagheck

[11] Patent Number: 5,294,198
[45] Date of Patent: Mar. 15, 1994

[54] INFRARED INSPECTION SYSTEM AND METHOD EMPLOYING EMISSIVITY INDICATIONS

[75] Inventor: Jerry G. Schlagheck, West Chester, Ohio

[73] Assignee: Cincinnati Electronics Corporation, Mason, Ohio

[21] Appl. No.: 769,430

[22] Filed: Oct. 1, 1991

[51] Int. Cl.$^5$ .............................................. G01N 25/72
[52] U.S. Cl. .................................... 374/4; 374/124; 374/128; 374/137; 374/126; 374/5; 250/332
[58] Field of Search ................... 374/4, 5, 6, 7, 126, 374/128, 124, 137; 364/557; 250/332

[56] References Cited

U.S. PATENT DOCUMENTS

| | | | |
|---|---|---|---|
| 3,392,282 | 7/1968 | Astheimer | 250/351 |
| 3,794,838 | 2/1974 | Weiss et al. | 250/352 |
| 3,889,053 | 6/1975 | Lloyd et al. | |
| 4,375,333 | 3/1983 | Clark et al. | 356/43 |
| 4,439,049 | 3/1984 | Hoogendoorn et al. | 374/5 |
| 4,463,437 | 7/1984 | Schenck et al. | 374/137 |
| 4,499,470 | 2/1985 | Stacey | 374/122 |
| 4,611,930 | 9/1986 | Stein | 374/126 |
| 4,634,294 | 1/1987 | Christol et al. | 374/124 |
| 4,647,220 | 3/1987 | Adams et al. | 374/5 |
| 4,705,945 | 11/1987 | Worcester | 250/352 |
| 4,768,158 | 8/1988 | Osanai | 374/5 |
| 4,818,118 | 4/1989 | Bantel et al. | 374/7 |
| 4,840,496 | 6/1989 | Elleman et al. | 374/124 |
| 5,032,727 | 7/1991 | Cox, Jr. et al. | 374/4 |
| 5,131,758 | 7/1992 | Heyman et al. | 374/4 |
| 5,133,605 | 7/1992 | Nakamura | 374/124 |
| 5,169,233 | 12/1992 | Montgomery et al. | 374/124 |

FOREIGN PATENT DOCUMENTS

| | | | |
|---|---|---|---|
| 0084374 | 7/1983 | European Pat. Off. | |
| 0075786 | 4/1984 | Japan | 374/126 |
| 2168494 | 6/1986 | United Kingdom | 374/5 |

OTHER PUBLICATIONS

Rucklidge, J., "A Beginner's Guide to Infra-Red Thermometers," Land Instruments, Inc. Tullytown, Pa., pp. 9.1-9.3 (1979).
Masi, C., "What Can Thermal Imaging Do For You," Test and Measurement World, May 1988.
X. Maldague et al., "Subsurface Flaw Detection in Reflective Materials by Thermal Transfer Imaging," Optical Engineering, Jan. 1991, vol. 30, No. 1, pp. 117-125.

Primary Examiner—William A. Cuchlinski, Jr.
Assistant Examiner—Diego F. F. Gutierrez
Attorney, Agent, or Firm—Lowe, Price, LeBlanc & Becker

[57] ABSTRACT

A unit having differing thermal emissivities at differing regions thereof is monitored with an infrared camera for deriving a signal having magnitudes representing infrared emission from multiple pixels in the camera field of view. A computer responsive to the signal (a) stores data representing emissivity and standard temperature of the unit at each of the pixels, (b) combines indications of the infrared emission from each pixel and the stored data representing emissivity of each pixel to derive an indication of monitored temperature of each pixel, (c) compares the stored data representing standard temperature of each pixel and the indications of monitored temperature of each pixel, and (d) derives an indication of the deviation between the magnitude of the standard temperature and monitored temperature at each pixel. In response to the indication of the deviation at each pixel, a property of the unit related to the deviations at the pixels is derived.

19 Claims, 6 Drawing Sheets

INFRARED INSPECTION SYSTEM AND METHOD EMPLOYING EMISSIVITY INDICATIONS

FIELD OF THE INVENTION

The present invention relates generally to apparatus for and method of determining the presence and location of defects in manufactured items, and more particularly, to such a method and apparatus wherein an infrared image of the device, while stimulated, is derived from an infrared image and compared with a standard temperature image.

BACKGROUND ART

Life-cycle methods have been previously used for determining the presence and location of defective parts and regions of a manufactured device by vibrating and temperature cycling the device for prolonged periods, typically about 48 hours. After the device has been life-tested by being vibrated and/or cyclically heated, it is inspected to determine defects by obtaining an infrared image of the device while the device is being stimulated. An infrared television camera supplies a signal to a color television monitor for deriving a multi-color image viewed by a human observer, who functions as an inspector for the device. Typically, hot and cold regions respectively appear on the monitor as the colors red and blue. The inspector is trained to recognize which areas should be red and which areas should be blue. Based on the inspector's training and the image on the monitor, the inspector decides whether a particular inspected device is defective or acceptable. In an automatic mode, a computer makes the decisions as to whether the device is acceptable.

In the prior art arrangement, the inspected life-tested device is environmentally stress screened by sine or random vibration, and/or by burn-in techniques. The environmental stress screening is used mainly to artificially improve reliability of a product by aging the product. However, the aging process actually reduces reliability because it fatigues marginal and sound parts of the device. Aging is the very characteristic which frequently accelerates wear of the product or device being tested or screened. Hence, with the prior art arrangement, there is a risk of damaging and weakening good parts and, in many cases, good parts are destroyed. Invariably, during this process, there is damage, to some degree, to all components having absolutely no flaw during manufacture.

The prior art arrangement is relatively expensive from initial capital and operational standpoints. The high capital cost is attributed to the expenses associated with the equipment for long term vibration, as well as heating and cooling of every produced device. Temperature testing employs heaters and associated cooling mechanisms, custom temperature fixtures and associated electronic hardware for each tested assembly. A factor in the capital expense of a typical prior art arrangement is that the required floor space is usually in excess of 200 square feet. The high operational expense results from operating the vibration as well as heating and cooling equipment, in addition to the relatively slow product throughput associated with the time required to conduct prolonged vibration and/or elevated thermal tests and/or temperature cycling. The need for a highly trained human inspector for each produced device adds a considerable operational expense. The tested device must be powered up during temperature cycling. In both cases (vibration and temperature), a fixture for the tested device is aged, causing constant maintenance of the test fixture.

It is, accordingly, an object of the present invention to provide a new and improved apparatus for and method of inspecting and analyzing manufactured devices in response to the infrared energy emitted from the device while it is being stimulated.

An additional object of the invention is to provide a new and improved apparatus for and method of inspecting and analyzing manufactured devices and determining the worthiness thereof without subjecting the device to prolonged vibration and/or temperature cycling so that the tested device is not prematurely aged due to the inspection process.

An additional object of the invention is to provide a new and improved apparatus for and method of inspecting a manufactured part in such a manner that the inspection time is considerably reduced relative to the prior art.

A further object of the invention is to provide a new and improved relatively inexpensive apparatus for and method of testing manufactured devices for defects.

A further object of the invention is to provide a new and improved method of and apparatus for more accurately determining minor and major fault defects in manufactured devices.

An additional object of the invention is to provide a new and improved apparatus for and method of inspecting manufactured device which is easily incorporated into production lines and requires relatively little space in such lines.

Scanned x-ray systems were also previously used to determine the presence of defects in manufactured devices. In such systems, the device is effectively scanned by an x-ray source. A human observer notes the presence of cracks or other abnormalities and defects from an x-ray image of the device. Such systems are expensive, and invasive of the device, as well as possibly the inspector and other personnel, with adverse effects on both.

An additional object of the invention is to provide a new and improved apparatus for and method of testing manufactured devices wherein the apparatus is completely passive to the product and personnel, so that there is no need for invasive devices such as x-rays.

SUMMARY OF THE INVENTION

In accordance with one aspect of the invention, an apparatus for analyzing a unit in the form of a device or a structure having differing thermal emissivities at differing regions comprises an infrared camera for monitoring infrared emission from the unit and for deriving a signal having magnitudes representing the infrared emission from multiple pixels in a field of view of the camera. A computer responsive to the signal includes: means storing data representing emissivity and standard temperature of the unit at each of the pixels. The stored emissivity and standard temperature data for some of the pixels of the unit differ from the stored emissivity and standard temperatures indication of others of the pixels of the unit. Indications of the infrared emission from the pixels and the stored data representing emissivity of the pixels are combined to derive an indication of monitored temperature of the pixels. The stored data representing standard temperature of each pixel are compared with the indications of monitored temperature of the pixels. An indication of the deviation between the magnitude of the standard temperature and monitored temperature at the pixels is derived. In response to the indication of the deviation at each pixel, an indication is derived of a property of the unit, related to the deviations at the pixels.

Preferably, the indication is derived in response to a deviation in excess of a predetermined value at any pixel to signal that the unit is unacceptable for its intended purpose. The signal is preferably derived for each pixel of a single analyzed unit at plural times. The computer derives the deviation indication for each pixel at each of the plural times and the properties indicated for the single analyzed unit in response to the deviation indication for each pixel at each of the plural times.

In accordance with another aspect of the invention, a unit in the form of a device or a structure having differing thermal emissivities at differing regions is analyzed by monitoring infrared emission from the unit with an infrared camera so the camera derives a signal having magnitudes representing the infrared emission from multiple pixels in a field of view of the camera. The signal is supplied to a computer storing data representing emissivity and standard temperature of the unit at each of the pixels. The stored emissivity and standard temperature data for some of the pixels of the unit differ from the stored emissivity and standard temperature indication of others of the pixels of the unit. The computer responds to the signal and the stored data by (a) combining indications of the infrared emission from the pixels and the stored data representing emissivity of the pixels to derive an indication of monitored temperature of the pixels, (b) comparing the stored data representing standard temperature of each pixel and the indications of monitored temperature of the pixels, and (c) deriving an indication of the deviation between the magnitude of the standard temperature and monitored temperature at the pixels. A property of the unit that is related to the deviations at the pixels is indicated in response to the indication of the deviation of the pixels.

In one preferred arrangement, the unit has a standard pixel with known radiation emissivity. The standard pixel is spatially displaced from the first pixels for which the deviation magnitudes are being derived. The camera detects the intensity of infrared radiation emitted from the first pixels and the standard pixel while the unit is at first and second displaced temperatures. The computer combines indications of (i) the detected intensity of infrared radiation emitted from the first pixels and the standard pixel while the unit is at the first and second displaced temperatures and (ii) the known emissivity of the standard pixel. The indications of (i) and (ii) are combined such that the first indication of the temperature of pixels is derived.

The method can be performed to derive the data representing the standard temperature for the first pixels by performing the steps of the previous paragraph on Q units having second pixels corresponding to the first pixels and further pixels having the known emissivity and corresponding with the standard pixels, where Q is at least several. Indications are derived of the detected intensities from the corresponding second pixels and the further pixels of the Q units. The computer combines the derived indications of the detected intensities from the corresponding second pixels and the further pixels of the Q units to derive the data representing the standard temperature of the first pixels.

The computer preferably derives the data representing the standard temperature for the first pixels in response to $$B = \frac{I_{T1}}{I_{STDT1} \, \epsilon_{STD}}$$

$$C = \frac{I_{T2}}{I_{STDT2} \, \epsilon_{STD}}$$

$$r(B, C) = \frac{\sum_{q=1}^{Q} |B_q - \overline{B}| \cdot |C_q - \overline{C}|}{Q \cdot S_B \cdot S_C}$$

where:
$I_{T1}$ = intensity of radiation from the second pixels at the first temperature
$I_{T2}$ = intensity of radiation from the second pixels at the second temperature
$I_{STDT1}$ = intensity of radiation from the further pixels at the first temperature
$I_{STDT2}$ = intensity of radiation from the further pixels at the second temperature
$\epsilon_{STD}$ = the known radiation emissivity
$Q$ = the number of the at least several units
$q$ = is successively each of $1, 2 \ldots Q$
$\overline{B}$ = average value of B for the Q units
$\overline{C}$ = average value of C for the Q units
$S_B$ = standard deviation of B for the Q units
$S_C$ = standard deviation of C for the Q units.

The steps are preferably performed on the first pixels of a monitored unit and on the standard pixel of the monitored unit. The computer preferably derives the indication of the temperature of the first pixels in response to $$r_{tested}(B, C) = \frac{|B_{test} - \overline{B}| \cdot |C_{test} - \overline{C}|}{S_B \cdot S_C}$$

where $$B_{test} = \frac{I_{T1(test)}}{I_{STDT1(test)} \, \epsilon_{STD}}$$

$$C_{test} = \frac{I_{T2(test)}}{I_{STDT2(test)} \, \epsilon_{STD}}$$

$I_{T1(test)}$ = intensity of radiation from the first pixels of the monitored unit at the first temperature
$I_{T2(test)}$ = intensity of radiation from the first pixels of the monitored unit at the second temperature
$I_{STDT1(test)}$ = intensity of radiation from the standard pixel of the monitored unit at the first temperature
$I_{STDT2(test)}$ = intensity of radiation from the standard pixel of the monitored unit at the second temperature.

The computer preferably derives indications of (a) the standard temperature for the first pixels in response to $B \cdot r(B,C)$ and (b) the monitored temperature for the first pixels in response to $B_{test} \cdot r_{tested}(B,C)$, and (c) the deviations between the indications of standard temperature for the first pixels and the monitored temperatures for the first pixels of the monitored unit.

The aforementioned method can be performed on a unit including plural components to detect the expected lifetime of the unit, wherein each of the components occupies a plurality of the first pixels and has known pixel locations on the unit. The camera monitors the intensity of infrared radiation emitted from the pixels forming the components while the components are stimulated to a higher temperature than ambient temperature of the unit. The computer responds to the radiation indications for the pixels of each particular component and an indication of the particular component radiation emissivity to derive an indication of expected operating temperature of each particular component. In response to the indication of expected operating temperature of each particular component and a stored value relating expected operating temperature of each particular component to the lifetime of the particular component, there is derived a second indication representing the expected lifetime of each particular component. The second indications for all of the components are combined to derive the indication of the unit expected lifetime. The temperature indication of each particular component is derived by combining the indications of (a) the monitored radiation intensity from all of the pixels occupied by the particular component and (b) the radiation emissivity of the pixels occupied by the particular component.

The above and still further objects, features and advantages of the present invention will become apparent upon consideration of the following detailed description of an embodiment thereof, especially when taken in conjunction with the accompanying drawings.

DESCRIPTION OF THE PREFERRED EMBODIMENT

Figure 1:
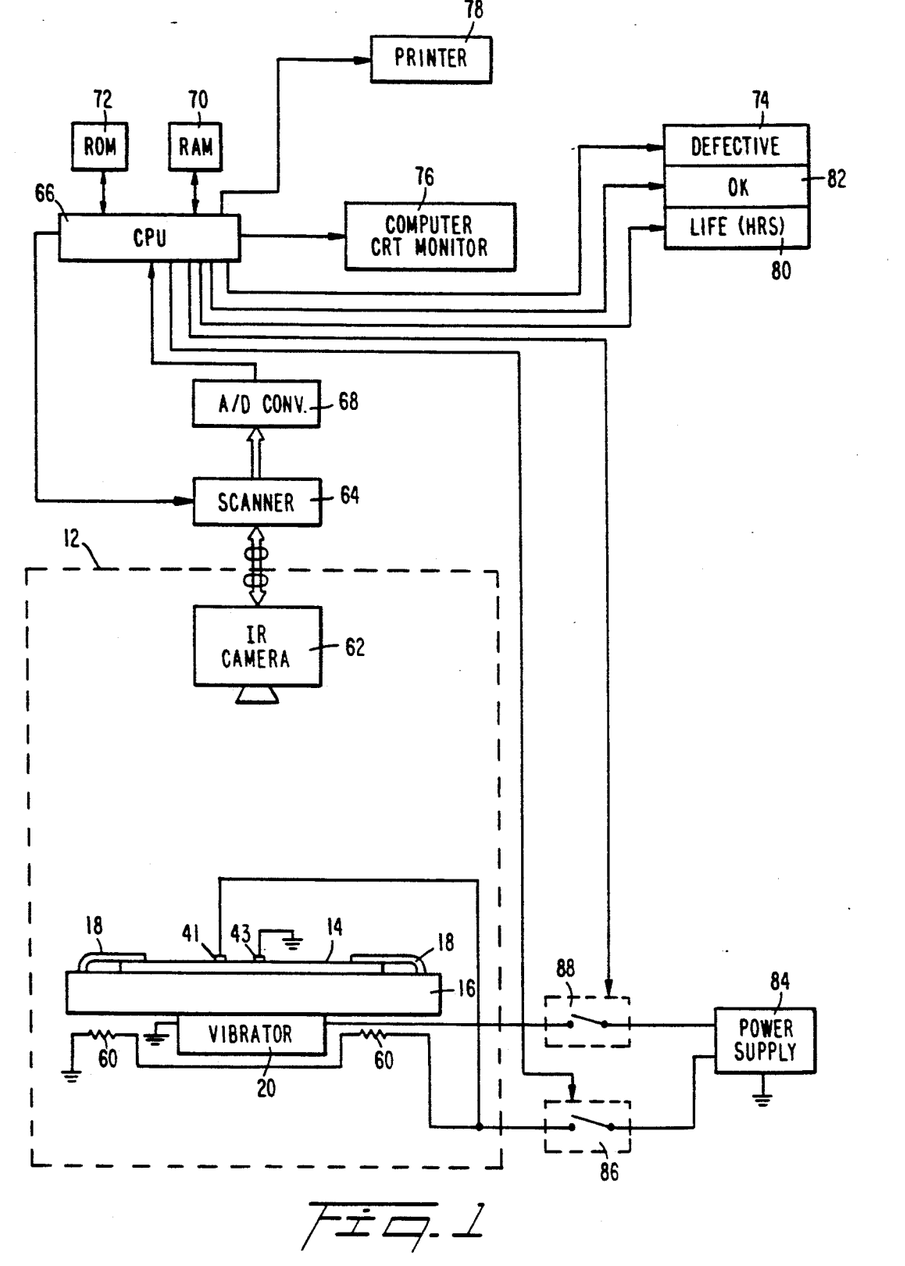
FIG. 1 is a schematic mechanical and electrical diagram of a preferred embodiment of the present invention.

Reference is now made to FIG. 1 of the drawing wherein a device to be tested is located in thermally stable chamber 12. In the specific embodiment described, the tested device is printed circuit assembly 14, FIG. 2, formed as a DC amplifier including transistors 16, 18 and 20, as well as resistors 21-32, all of which are connected to each other by aluminum strips 40-50 deposited on dielectric substrate 52, which also includes target 54 fabricated of a material having a known, precise and stable thermal emissivity coefficient. Printed circuit assembly 14 is mounted on mounting fixture 16 by spring fingers 18. Mounting fixture 16 is mechanically connected to mechanical vibrator 20 and placed in proximity to electric heating devices 60, located within chamber 12. (While device 60 is shown as a resistance heater, it is to be understood that separate heaters are not necessary and that the function of heaters 60 is preferably performed by electric devices in chamber 12 that are turned on and off during operation of the device.)

Figure 2:
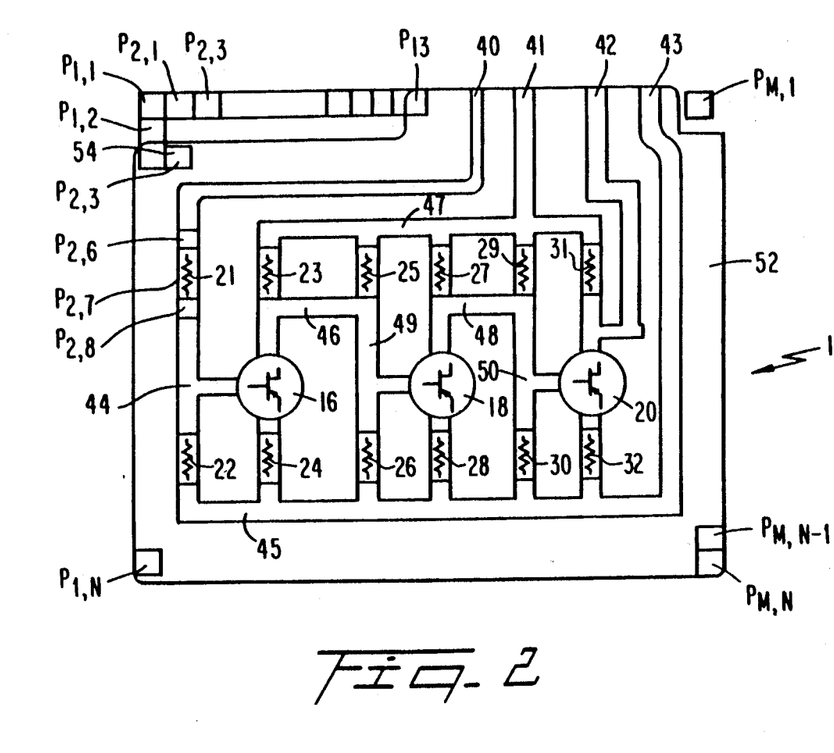
FIG. 2 is a view of a printed circuit assembly of the type monitored with the apparatus of FIG. 1.

Infrared radiation radiated from the face of printed circuit assembly 14 opposite from the face of the printed circuit assembly in contact with fixture 16 is monitored by infrared camera 62, mechanically driven up and down relative to printed circuit assembly 14, as well as in X and Y coordinate directions in a plane at right angles to the exposed face of printed circuit assembly 14. Such movements of camera 62 are provided by conventional drive structures (not shown). Camera 62 also includes a zoom lens feature to enable different regions of printed circuit assembly 14 to be monitored with greater resolution than other regions of the printed circuit assembly. While camera 62 is monitoring printed circuit assembly 14 the camera is maintained in a stationary condition.

Camera 62 derives a set of signals, one for each region, i.e. pixel, of printed circuit assembly 14 and indicative of the intensity of the infrared radiation emitted from the pixel. Camera 62 is preferably of a type including a separate target for each pixel on the exposed face of printed circuit assembly 14. The intensity of the infrared radiation emitted from each pixel of printed circuit assembly 14 is determined by supplying the signal from each target region of infrared camera 62 to multiplexing scanner 64, addressed in a conventional manner by signals from central processing unit (CPU) 66. Scanning multiplexer 64 supplies a sequence of signals at displaced time intervals to analog to digital converter 68; the signals represent the intensity of infrared radiation emitted from each pixel of printed circuit assembly 14. Converter 68 supplies digital signals to CPU 66. The digital signals supplied by converter 68 are routed by CPU 66 to random access memory (RAM) 70. CPU 66 includes an internal program to control the flow of data from converter 68 to RAM 70 and from RAM 70 back to the CPU, as described infra. CPU 66 is also responsive to table look-up information stored in read-only memory (ROM) 72.

CPU 66 responds to the signals from infrared camera 62 indicative of the infrared emission from the pixels of printed circuit assembly 14, as well as signals from RAM 70 and ROM 72, to derive signals indicative of the temperature of each pixel. The signals indicative of each pixel temperature are combined with standard values for the temperature at each pixel to determine if a particular pixel has an excessively high or low temperature while printed circuit assembly 14 is being vibrated by vibrator 20 and heated by heaters 60. In a preferred embodiment, 80 milliseconds are required to examine all of the pixels of printed circuit assembly 14. One such 80 milliseconds time interval is referred to herein in as a scan period. Each printed circuit assembly 14 is examined over at least several scan periods, typically for about one to two seconds. If any pixel in any of the scan periods has a temperature above or below a predetermined value, CPU 66 derives a signal indicating the printed circuit assembly as being defective; such a signal after being stored in RAM 70 is supplied to DEFECTIVE visual indicator output 74 and to printer 78 with an indication of the identity of the defective assembly number.

The deviation in temperature of each pixel from the standard value therefore is supplied, at the end of each scan period, by CPU 66 to computer cathode ray tube (CRT) monitor 76. Monitor 76 can be a black and white monitor, showing pixel deviation in gray-scale so there is a spatial correlation between the image on the monitor and the pixels of printed circuit assembly 14 monitored by camera 62. Alternatively, monitor 76 can be a color display wherein pixels having temperatures in excess of and less than the standard values are respectively indicated by differing shades of red and blue; the intensity of the red and blue pixel images on CRT monitor 76 increases as the temperature deviates by greater amounts from the standard value therefore. The gray scale values are converted into color intensities by a look-up table included in ROM 72. Computer CRT monitor 76 thus provides a spatial representation of the pixels on printed circuit assembly 14 that deviate in temperature from the standard temperature of the pixel. If a particular pixel of printed circuit assembly 14 is at a temperature exactly equal to the standard temperature for that pixel, a neutral color appears at the corresponding pixel on monitor 76.

CPU 66 also responds to the signals from IR camera 62 and ROM 72 to derive indications of the expected life of each component on printed circuit assembly 14. Each component occupies at least several predetermined pixels on printed circuit assembly 14. The average temperature of the pixels on printed circuit assembly 14 where the components, e.g., transistors 16–20 and resistors 21–32, are located is determined from the intensity of the infrared radiation monitored by camera 62. From the temperatures resulting from the monitored infrared energy for the pixels of a particular component and stored values in ROM 72, the expected life of a particular component is determined. The expected component life is compared with a minimum life (in hours) of the component. If the comparison indicates the expected component life is less than the minimum required component life, the printed circuit assembly is indicated as being defective and printer 78 is activated to indicate the particular component is defective. The component can, thereby, easily be removed and the printed circuit assembly re-worked appropriately.

The life of printed circuit assembly 14 is determined by CPU 66 in response to signals from RAM 70 and ROM 72 by combining the indications of the expected life of all of the components. The expected life of the printed circuit assembly thus determined is compared by CPU 66 with a minimum acceptable expected printed circuit assembly life. If CPU 66 determines that the life of printed circuit assembly 14 is less than a predetermined duration, CPU 66 supplies a signal to DEFECTIVE visual indicator output 74 and to printer 78. The expected life of printed circuit assembly 14 is supplied by CPU 66 to printer 78, as well as to LIFE numerical read-out 80. If all of the pixels, components and printed circuit assembly 14 as a whole have expected temperature values and lifetimes in conformance with established standards, CPU 66 supplies a signal to OK output 82, as well as to printer 78.

CPU 66 responds to its internal program to control the application of energy from power supply 84 to vibrator 20 and heater 60. To this end, CPU 66 supplies separate signals to contacts 86 and 88, causing closure thereof to connect power supply 84 to heaters 60 and vibrator 20, respectively. When contacts 86 are closed, power is supplied to aluminum strips 41 and 43 on printed circuit assembly 14 to stimulate operation of the amplifier on printed circuit assembly 14. Connections are made to strips 41 and 43 by machinery (not shown) automatically controlling conveying of printed circuit assemblies 14 onto vibrator 16 or such connections can be made manually.

In a manufacturing facility, printed circuit assemblies 14 are automatically supplied to fixture 16 by a conveyor structure (not shown). Each printed circuit assembly 14 includes a standard bar code for identification purposes to enable data to be collected and stored by CPU 66 and RAM 70 for all of the monitored printed circuit assemblies. Alternatively, the printed circuit assemblies can be manually inserted on spring fingers 18 of fixture 16.

Standards for the temperature at each pixel of the monitored, manufactured printed circuit assemblies are established by supplying an appropriate number, e.g., 20, satisfactory life-tested printed circuit assemblies identical to the monitored printed circuit assemblies to fixture 16. The intensity of the infrared radiation emitted from each pixel for each of the life-tested assemblies is monitored by infrared camera 62 and coupled to CPU 60, thence to RAM 70. The average value of the intensity at each pixel for all of the life-tested printed circuit assemblies is determined and compared with the intensity of the intensity of the infrared radiation emitted from standard target material 54. The emissivity at each pixel is thereby determined. The emissivity values for the pixels are combined with the radiation intensity indications from the monitored printed circuit assemblies to determine the temperature at each monitored pixel of each tested printed circuit assembly.

Prior to considering the computer program stored by CPU 66 to determine the properties of printed circuit assembly 14 and supply signals indicative thereof to output devices 70 and 74–82, further consideration is given to FIG. 2. In FIG. 2, pixels $P_{x,y}$ are illustrated as being superimposed on printed circuit assembly 14 such that pixel $P_{l,l}$ is in the upper left-hand corner and pixel $P_{m,n}$ is in the lower right-hand corner. In one preferred embodiment, $M=192$, and $N=100$ so that there are 19,200 square, equal-area pixels in the field of view of infrared camera 62. Camera 62 includes a scanning detector for each of the 19,200 pixels. In the simplified situation illustrated in FIG. 2, target region 54 having a precise, known stable thermal emissivity is located at pixel $P_{2,3}$. Resistor 21, having a rectangular shape in the field of view of camera 62, occupies pixels $P_{2,6}$-$P_{2,8}$. The remaining components, i.e., transistors and resistors, on printed circuit assembly 14 occupy precise pixels so that the areas thereof in the field of view of camera 62 are known.

Figure 3A:
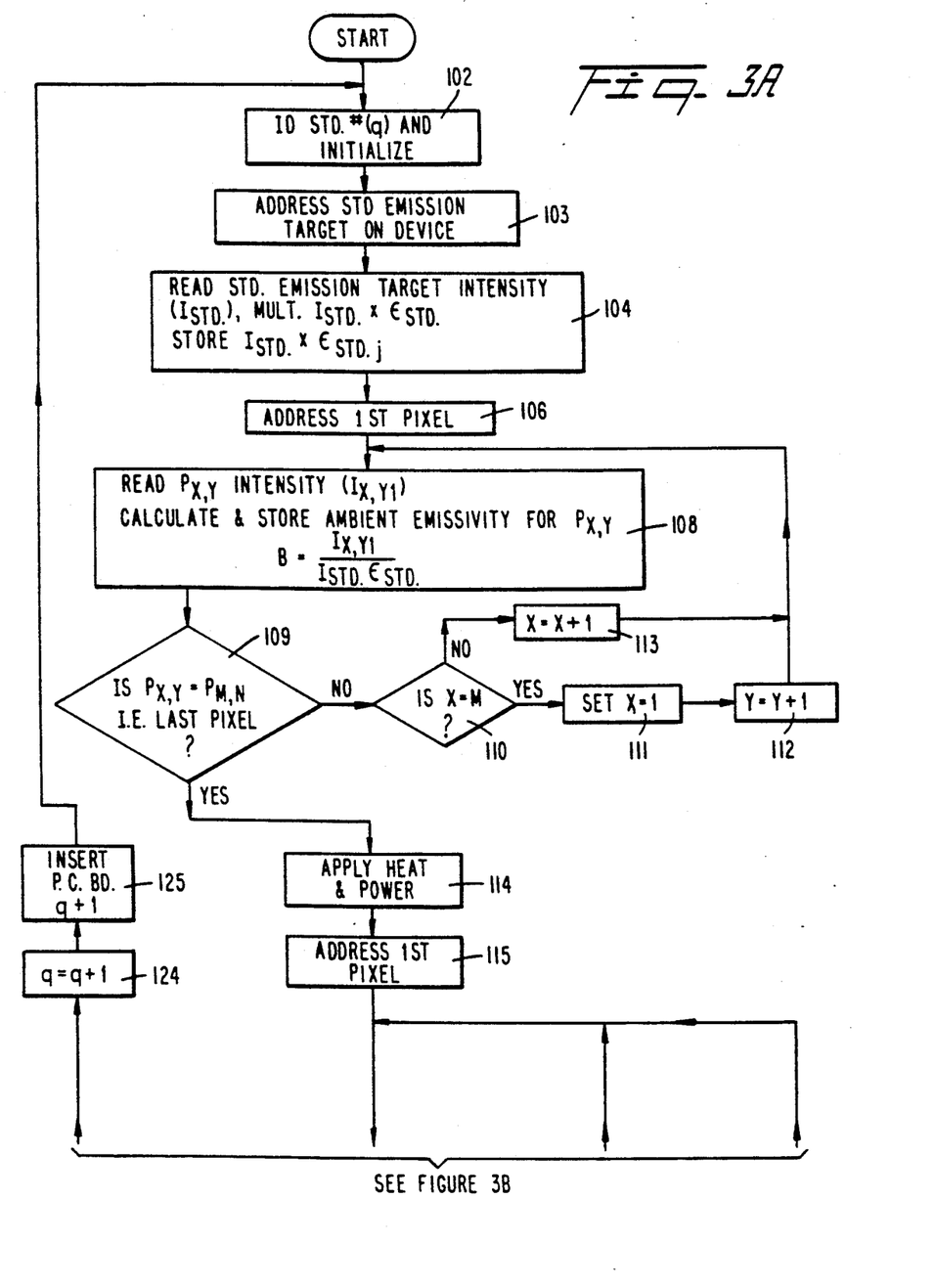
FIGS. 3A and 3B show a flow diagram of operations performed by the apparatus of FIG. 1 on printed circuit assemblies that have been life-tested to enable the standard data to be derived.
Figure 3B:
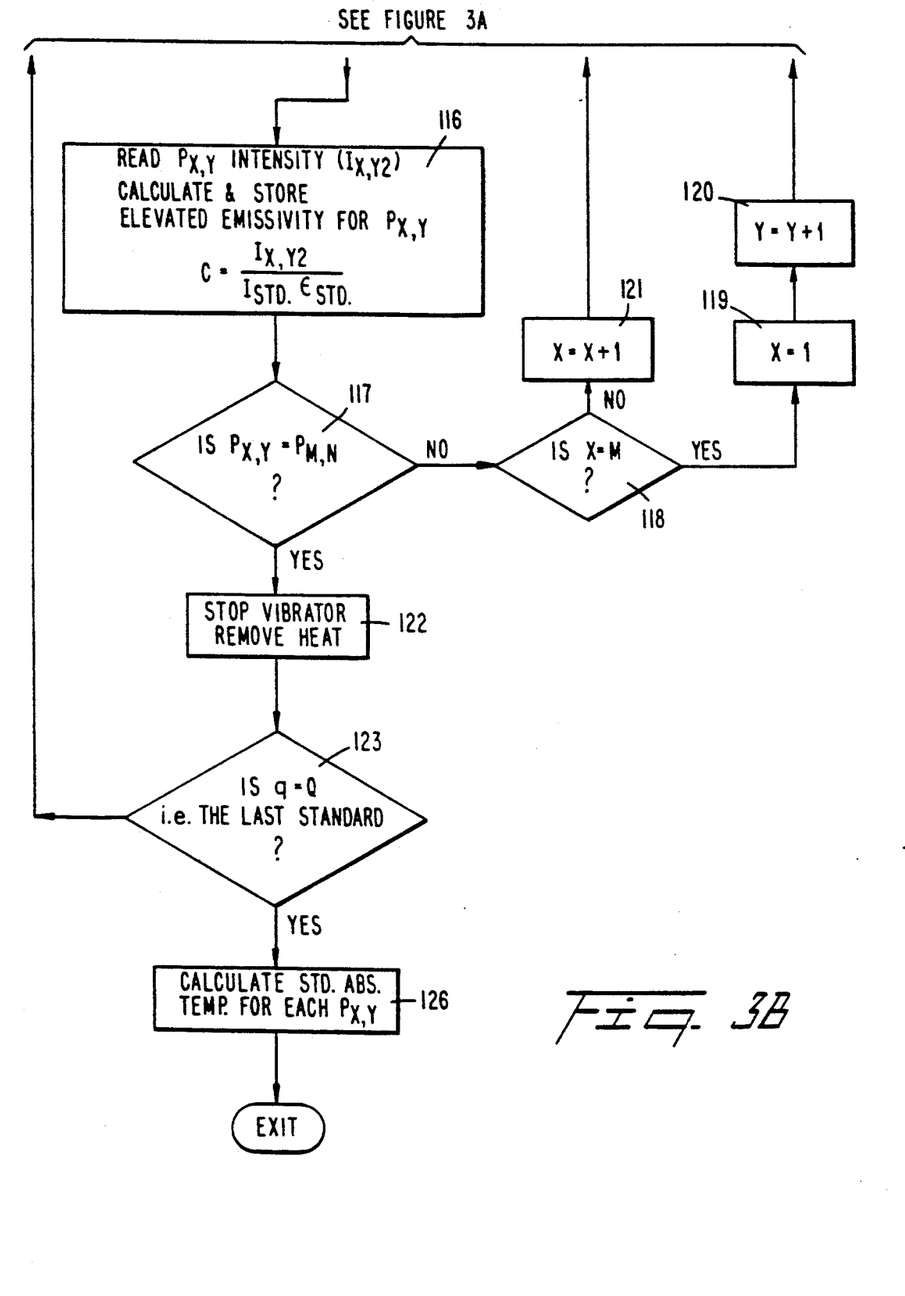

Reference is now made to FIGS. 3A and 3B of the drawings, a showing a flow diagram of operations and computations performed by the apparatus to determine standard emissivity of each pixel on each of the life-tested printed circuit assemblies, as well as the standard absolute temperature of each pixel of a printed circuit assembly during operation. The operations of FIGS. 3A and 3B are performed in sequence on each of many, e.g., 20, life-tested printed circuit assemblies identical to the printed circuit assemblies of FIG. 2. As indicated supra, the life-tested printed circuit assemblies are supplied in sequence to fixture 16.

The first operation 102 of the standard computation, after a life-tested printed circuit assembly has been loaded onto fixture 16, is to identify the number of the life-tested printed circuit assembly being monitored and to initialize operations. The identification of the life-tested printed circuit assembly is determined by directing infrared camera 62 at the region on the printed circuit assembly where the bar code identification (not shown) for the printed circuit assembly is located. The bar code information is read by camera 62 into an appropriate address in RAM 70 under the direction of CPU 66. CPU 66 then supplies a signal to command closure of switch 88 causing vibrator 20 to be activated by power supply 84.

Computer 66 then (during operation 103) directs infrared camera 62 to pixel $P_{2,3}$ where standard emission target 54 is located. The intensity of the infrared radiation from target 54 while printed circuit assembly 14 is at ambient temperature, $I_{STD(AMB)}$, is then determined by IR camera 62 deriving an analog signal indicative of this value. The signal for target 54 derived by camera 62 is supplied by scanner 64 to analog-to-digital converter 68. The digital output of converter 68 is supplied by CPU 66 to a designated address in RAM 70. The intensity of the radiation emitted by target 54, $I_{STD(AMB)}$, stored in RAM 70 is combined with the known radiation emissivity of target 54, as stored in ROM 72, $\epsilon_{STD}$. CPU 66 responds to $I_{STD(AMB)}$ and $\epsilon_{STD}$ to derive the product $I_{STD}\epsilon_{STD}$. These steps are performed during operation 104.

Then (during operation 106) the intensity of the infrared radiation from the first pixel of the printed circuit assembly while the assembly is at ambient temperature is determined. To these ends, CPU 66 supplies a signal to scanner 64 to command read-out of infrared camera 62 from pixel $P_{13,1}$ for printed circuit assembly 14.

The computer program then advances to operation 108, during which infrared camera 62 is commanded to read the intensity $I_{x,y(AMB)}$ of the infrared energy emitted from pixel $P_{x,y}$ while assembly 14 is at ambient temperature. Initially, pixel $P_{x,y}$ is pixel $P_{13,1}$ as a result of the address supplied by CPU 66 to scanner 64. The ambient infrared intensity from each of the various pixels is read in sequence with the values of x increasing until the last value of x=M is reached; then CPU 66 increments y to command scanner 64 to read pixel $P_{1,2}$. The intensity of the infrared energy emitted from all of the pixels is read by camera 62 and stored in designated addresses of RAM 70. The scanning steps are indicated by operations 109, 110, 111, 112 and 113. During operations 112 and 113, the values of x and y are incremented by 1 to provide shifts in the values of x and y.

A measure of the temperature of each pixel while printed circuit assembly 14 is at ambient temperature is calculated during operation 108, after the intensity of the infrared energy for a particular pixel has been determined in accordance with:

$$B = \frac{I_{x,y(AMB)}}{I_{STD(AMB)} \epsilon_{STD}} \quad (1)$$

All of operations 102-108 are performed at ambient temperature in chamber 12. After operation 109 has determined that the last pixel of a particular life-tested printed circuit assembly has been read by infrared camera 62, the program advances to operation 114 during which CPU 66 commands closure of contacts 88 causing current to be supplied by power supply 84 to heaters 60, as well as strips 41 and 42. This causes heating and the application of power to the life-tested printed circuit assembly in the field of view of infrared camera 62. Heaters 60, when energized, typically raise the temperature of the printed circuit assembly 5° C.

CPU 66 then (during operation 115) commands scanner 64 to cause IR camera 62 to address standard pixel 54, followed by the first pixel $P_{13,1}$ on the life-tested printed circuit assembly being examined. After operation 115, CPU 66 commands IR camera 62 to read the intensity of the radiation from the multiple pixels of printed circuit assembly 14 in the same manner as described for ambient temperature operations; operations 116-121. During operation 116, the elevated temperature of each monitored pixel while the printed circuit assembly is at an elevated temperature is determined in accordance with:

$$C = \frac{I_{x,y(AMB+\delta T)}}{I_{STD(AMB+\delta T)} \epsilon_{STD}} \quad (2)$$

where: $I_{x,y(AMB+\delta T)}$=the intensity of infrared radiation from pixel x,y at the elevated temperature of printed circuit assembly 14; and $I_{STD(AMB+\delta T)}$=the intensity of infrared radiation from target 54 at the elevated temperature of printed circuit assembly 14.

The values of B and C as calculated by CPU 66 during operations 108 and 116 are stored in designated addresses of RAM 70.

After the last pixel of a particular life-tested printed circuit assembly has been read, as determined during operation 117, the program advances to operation 122 during which CPU 66 commands contacts 86 and 88 to open so vibrator 20 and heaters 60 are de-energized. After operation 122, the program advances to program 123, when a determination is made as to whether the particular life-tested printed circuit assembly is the last life-tested assembly to be analyzed to determine standard temperature values for each pixel. In response to operation 123 indicating that there are remaining life-tested printed circuit assemblies to be monitored to define the standard temperature values, the program advances to operation 124, when the number (q) of the life-tested printed circuit assembly is incremented by 1. Then, the program advances to operation 125 when a command is given to insert a different life-tested printed circuit assembly into fixture 16. After operation 125, the program returns to operation 102 and the previously described sequence is repeated until all of the life-tested printed circuit assemblies used to accumulate the standard temperature data have been monitored by infrared camera 62.

In response to operation 123 indicating that the last life-tested printed circuit assembly (Q) forming the standard has been monitored by camera 62, i.e., q=Q, the program of CPU 66 advances to operation 126. During operation 126, the absolute temperature for each pixel of all of the life-tested monitored printed circuit assemblies is calculated. To determine the standard absolute temperature for each pixel, a correlation correction coefficient for the ambient and elevated temperatures of printed circuit assembly 14 is determined for each pixel in accordance with:

$$r(B, C) = \frac{\sum_{q=1}^{Q} |B_q - \bar{B}| \cdot |C_q - \bar{C}|}{Q \cdot S_B \cdot S_C} \quad (3)$$

where Q, B and C have previously been defined, $\bar{B}$=the average value of B at the particular pixel for all of the Q life-tested printed circuit assemblies, $\bar{C}$=the average value of C at the particular pixel for all of the Q life-tested printed circuit assemblies, $S_B$=the standard deviation of the values of B at the particular pixel for the Q life-tested printed circuit assemblies, and $S_C$=the standard deviation of the values of C at the particular pixel for the Q life-tested printed circuit assemblies.

The corrected absolute temperature for each pixel is then computed as:

$$TC = B \cdot r(B,C) \quad (4)$$

Then, during operation 126, a gray-scale correction correlation factor is determined for each pixel in accordance with:

$$\text{Gray-scale} = \frac{(TU - TL)}{\text{Number of gray-scale steps}} \quad (5)$$

where: TU is an upper temperature detection limit of infrared camera 62, and
TL is a lower temperature detection limit for infrared camera 62.

Typically, TU=50° C., TL=20° C., and the number of gray-scale steps is 256.

Then, during operation 126, the absolute temperature value for each pixel is determined as:

$$Tgs = (TC \cdot gray\text{-}scale)TL \quad (6)$$

The values of Tgs for each pixel, after being calculated by CPU 66, are stored in designated addresses of RAM 70.

After operation 126, the standard computation program is exited. Data resulting from the standard computation program stored in RAM 70 are combined with signals from infrared camera 62 when the camera is viewing printed circuit assemblies 14 in chamber 12 to determine the acceptability and lifetime of the printed circuit assemblies. The operations and computations required to determine the acceptability and lifetime (in hours) of manufactured printed circuit assemblies, without going through a life-test, are illustrated in FIG. 4.

Figure 4A:
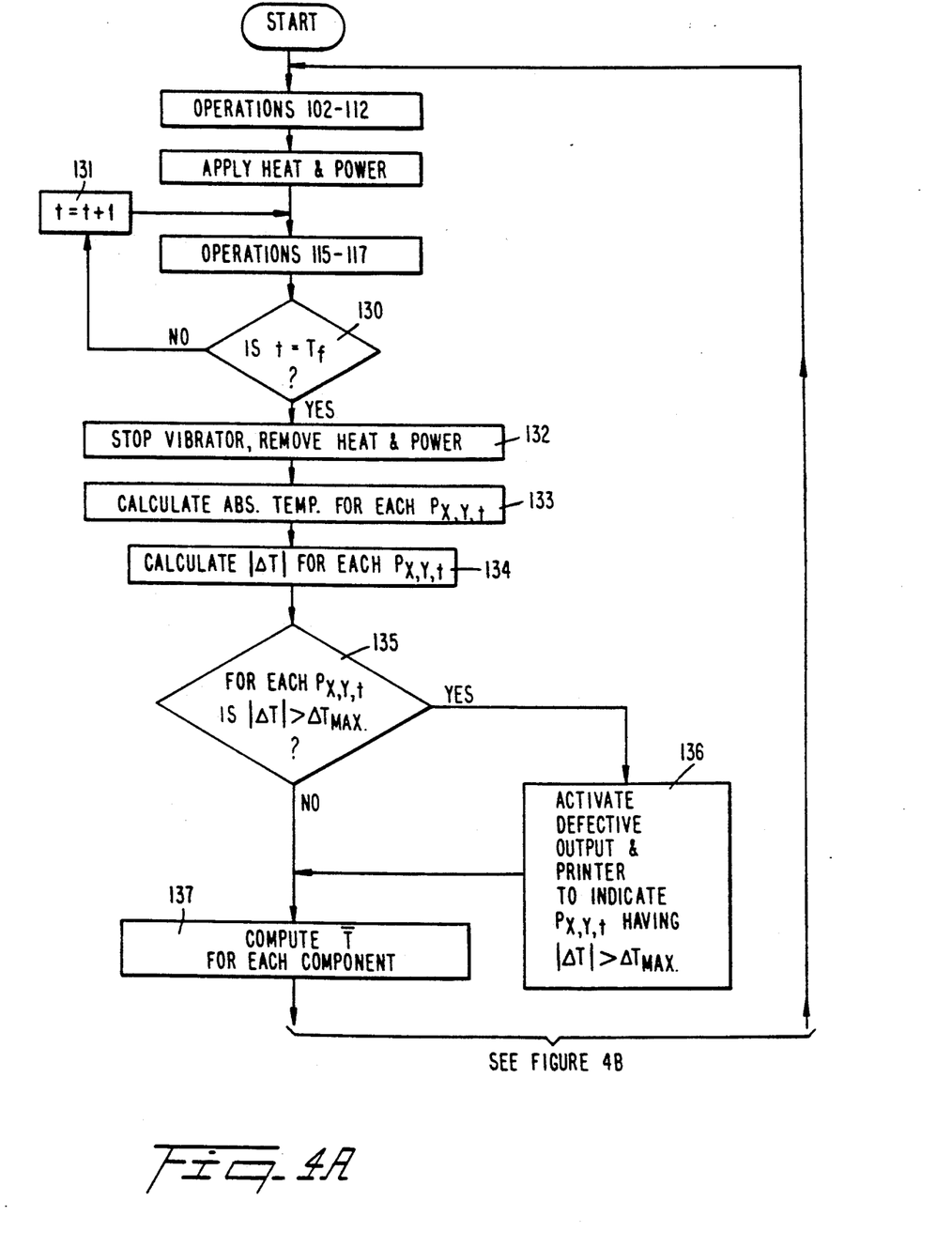
FIGS. 4A and 4B show a flow diagram of operations performed by the apparatus of FIG. 1 on printed circuit assemblies being tested to determine if the printed circuit assemblies are acceptable and the expected life of the assemblies.
Figure 4B:
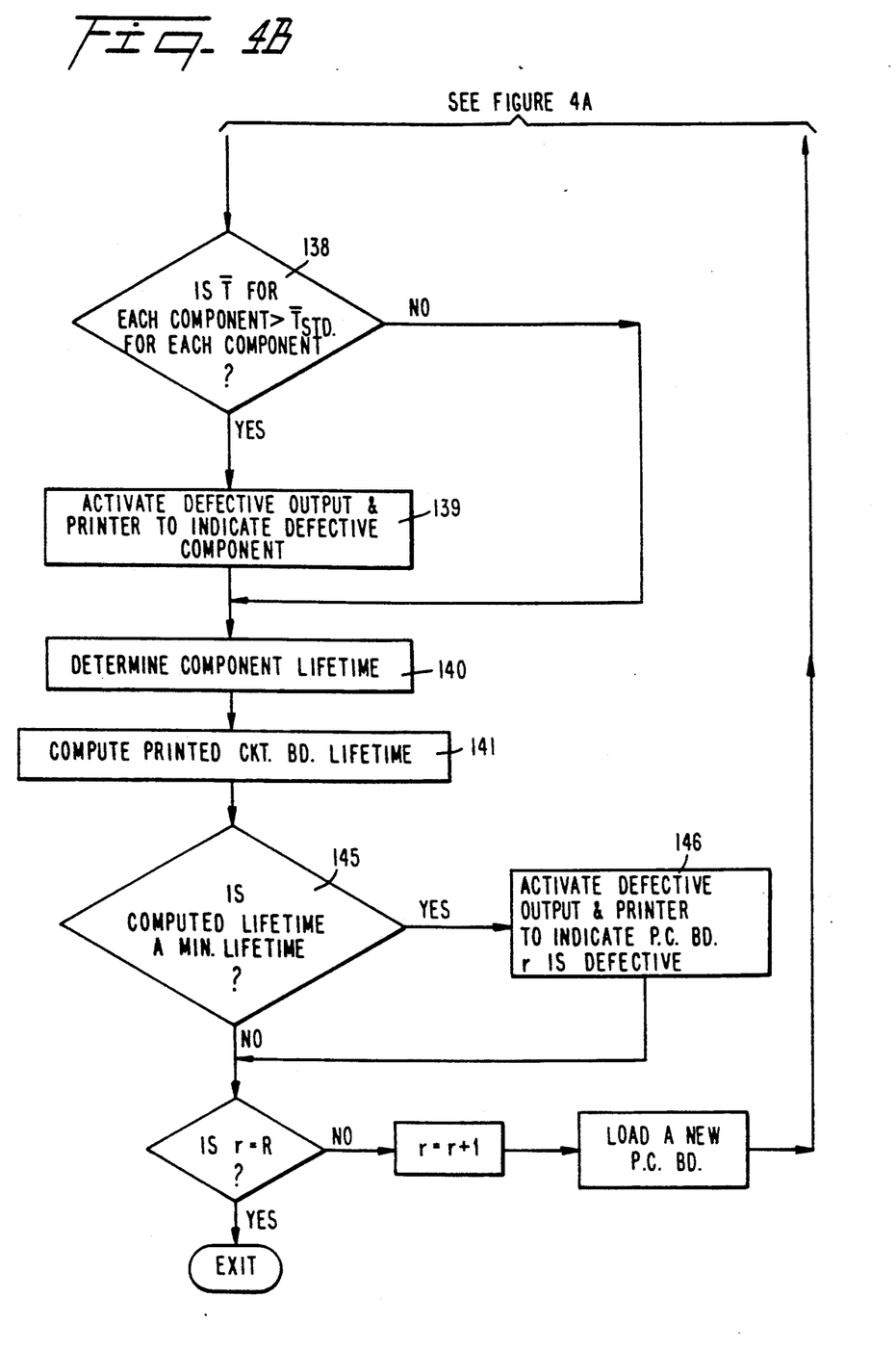

FIG. 4 is a flow diagram of operations performed by the apparatus of FIG. 1 on printed circuit assemblies 14 during production to determine whether the printed circuit assembly is defective, whether components on the printed circuit assembly are defective, and the life of the printed circuit assembly. After a printed circuit assembly has been loaded onto fixture 16 and while the printed circuit assembly is subjected to vibration for a few seconds, the intensity of infrared radiation from each pixel on the printed circuit assembly is determined at ambient conditions, in the same manner as discussed supra, for operations 102-112. Heat and power are then applied to the vibrating printed circuit assembly by energizing heaters 60 and connecting power supply voltage to aluminum stripes 41 and 43 on printed circuit assembly 14, as described supra for operation 114. The intensity of infrared radiation emitted from each of the pixels of the tested printed circuit assembly is then monitored during each of several scanning periods. During one of the scanning periods, intensity is monitored in the same manner as indicated supra in connection with operations 115-117. After each scanning period, a determination is made during operation 130 as to whether the last scanning period, $T_F$, has been reached for each particular printed circuit assembly being monitored. If the last scanning period has not been reached, the scanning period value, t, is incremented during operation 131 and the intensity of the infrared radiation from each of the pixels is again determined. Each of the values of radiation intensity for each of the pixels for each of the scanning periods is stored in RAM 70.

In response to operation 130 indicating completion of the last scan period, i.e., t=$T_F$, vibrator 20 and heaters 60 are de-energized and power is removed from strips 41 and 43 during operation 132. Fixture 16 is thus prepared to receive another printed circuit assembly.

Then, during operation 133, the absolute temperature for each pixel for each scanning period of the tested device is determined by using a similar set of equations as used to provide a measure of the absolute temperature of each pixel of the standard. The values of B and C for each of the pixels and all of the scanning periods of each manufactured, tested printed circuit assembly are determined in accordance with Equations (1) and (2). The correlation correction coefficient for each pixel and all of the scanning periods (t) of each tested printed circuit assembly is determined as:

$$r_{tested}(B, C) = \frac{|B_t - B| \cdot |C_t - C|}{S_B \cdot S_C} \quad (7)$$

where:
$B_t$ is the value of B for the pixel during scanning period t,
$C_t$ is the value of C for the pixel during scanning period t, and
$\overline{B}, \overline{C}, S_B$ and $S_C$ are determined during the operations of FIG. 3.

The absolute temperature value for each tested pixel during each scan period is determined from the values of $r_{tested}(B,C)$ and B for the tested pixel in accordance with:

$$T_{test} = B_t r_{test}(B,C)(Gray\text{-}scale) + TL \quad (8)$$

After the absolute temperature for each pixel during each scan period is determined, a measure of the deviation of the temperature for each pixel ($T_{test}$) from the desired value therefore (Tgs), as determined during the operations of FIG. 3, is made during operation 134 in accordance with $$|\Delta T| = |Tgs - T_{test}| \quad (9).$$

A determination is then made during operation 135 as to whether $|\Delta T|$ is greater than $\Delta T_{max}$ (where $\Delta T_{max}$ is a predetermined value stored in ROM 72 for each pixel and may differ from pixel to pixel) for each pixel during each scanning period. In response to operation 135 indicating that $|\Delta T|$ for a particular pixel during a particular scan period exceeds $\Delta T_{max}$ DEFECTIVE output 74 is energized and printer 78 is activated to indicate which pixel is defective during which scan period; these steps are performed during operation 136.

After operation 136 or in response to operation 135 providing a "no" result, the average temperature for each component on printed circuit assembly 14 is calculated during operation 137. The average temperature for each component is computed by determining the temperature during the last scan period, $T_F$, of each pixel occupied by the component. The temperatures at all of the pixels where a particular component is located are added and divided by the number of pixels the component occupies to determine average component temperature. The thus-determined component temperature value is increased to the expected operating ambient temperature of printed circuit assembly 14, in use. The expected temperature for each component is then compared with a standard maximum temperature for each component, stored in ROM 72; these steps are indicated by operation 138. In response to operation 138 indicating that a particular component has an expected operating temperature in excess of the maximum operating temperature for that component, the program advances to operation 139, during which DEFECTIVE output 74 is energized and printer 78 is activated to indicate the defective component on printed circuit assembly 14.

After operation 139 or a "no" response from operation 135, the lifetime of each component is determined during operation 140 by supplying the indication of component operating temperature calculated during operation 137 to a look-up table in ROM 72. The look-up table correlates the life of each component in hours, as determined from the component manufacturer, with expected operating temperature.

The lifetime of printed circuit assembly 14 is then computed during operation 141 by combining the component lifetimes derived during operation 140 in accordance with:

$$R_e = R_1 \cdot R_2 \cdot R_3 \ldots (etc) \tag{10}$$

where:

$R_1$ is a measure of the lifetime of a first component on printed circuit assembly 14;

$R_2$ is a measure of the lifetime of a second component on printed circuit assembly 14; and $R_3$ is a measure of the lifetime of a third component on printed circuit assembly 14.

The value computed during operation 141 is supplied, with the number of the printed circuit assembly, to printer 78 and then compared during operation 145 with a minimum lifetime for assembly 14. In response to the computed lifetime being less than the minimum lifetime value stored in RAM 72, DEFECTIVE output 74 is energized during operation 146.

After operation 146 or a "no" from operation 145, the program advances to operation 142 when a determination is made as to whether the printed circuit assembly just previously monitored is the last printed circuit assembly in the line. In response to a "yes" being derived during operation 142, the program is exited. In response to a "no" being derived during operation 142, the number of the printed circuit assembly handled is incremented during operation 143. Then, a new printed circuit assembly to be monitored is loaded onto fixture 16, as indicated by operation 144. The new printed circuit assembly is loaded automatically in the preferred embodiment, although such loading can be manual, in which case a visual signal is supplied to an operator by the apparatus illustrated in FIG. 1.

While there has been described and illustrated one specific embodiment of the invention, it will be clear that variations in the details of the embodiment specifically illustrated and described may be made without departing from the true spirit and scope of the invention as defined in the appended claims.

I claim:

1. Apparatus for analyzing a unit in the form of a device or a structure having differing thermal emissivities at differing regions thereof comprising an infrared camera for monitoring infrared emission from the unit and for deriving a signal having magnitudes representing the infrared emission from multiple pixels in a field of view of the camera, a computer responsive to the signal including: means storing data representing emissivity and standard temperature of the unit at each of the pixels, the stored emissivity and standard temperature data for some of the pixels of the unit differing from the stored emissivity and standard temperature indication of others of the pixels of the unit, means for: (a) combining indications of the infrared emission from the pixels and the stored data representing emissivity of the pixels to derive an indication of monitored temperature of the pixels, (b) comparing the stored data representing standard temperature of each pixel and the indications of monitored temperature of the pixels, and (c) deriving an indication of the deviation between the magnitude of the standard temperature and monitored temperature at the pixels; and means responsive to the indication of the deviation at each pixel for indicating a property of the unit, the property being related to the deviations at the pixels.

2. The apparatus of claim 1 wherein the means for indicating includes a two-dimensional display for displaying an image of the deviation at each pixel, the image spatially corresponding with an image of the unit.

3. The apparatus of claim 2 wherein the means for indicating responds to a deviation in excess of a predetermined value at any pixel for signaling that the unit is unacceptable for its intended purposes.

4. The apparatus of claim 1 wherein the signal is derived for each pixel of a single analyzed unit at plural times, the computer deriving the deviation indication for each pixel at each of the plural times, the property indicating means for the single analyzed unit responding to the deviation indication for each pixel at each of the plural times.

5. A method of analyzing a unit in the form of a device or a structure having differing thermal emissivities at differing regions thereof comprising monitoring infrared emission from the unit with an infrared camera so the camera derives a signal having magnitudes representing the infrared emission from multiple pixels in a field of view of the camera, supplying the signal to a computer storing data representing emissivity and standard temperature of the unit at each of the pixels, the stored emissivity and standard temperature data for some of the pixels of the unit differing from the stored emissivity and standard temperature indication of others of the pixels of the unit, the computer responding to the signal and the stored data by (a) combining indications of the infrared emission from the pixels and the stored data representing emissivity of the pixels to derive an indication of monitored temperature of the pixels, (b) comparing the stored data representing standard temperature of each pixel and the indications of monitored temperature of the pixels, and (c) deriving an indication of the deviation between the magnitude of the standard temperature and monitored temperature at the pixels; responding to the indication of the deviation at the pixels for indicating a property of the unit that is related to the deviations at the pixels.

6. The method of claim 5 wherein the pixels for which the deviation magnitudes are derived are first pixels, the unit having a standard pixel with known radiation emissivity, the standard pixel being spatially displaced from 7. The method of claim 6 wherein the method is performed to derive the data representing the standard temperature for the first pixels by performing said steps of claim 6 on Q units having second pixels corresponding to said first pixels and further pixels having the known emissivity and corresponding with said standard pixels, where Q is at least several, deriving indications of the detected intensities from the corresponding second pixels and the further pixels of the Q units, the computer combining the derived indications of the detected intensities from the corresponding second pixels and the further pixels of the Q units to derive the data representing the standard temperature of the first pixels.

8. The method of claim 7 wherein the computer derives the data representing the standard temperature for the first pixels in response to $$B = \frac{I_{T1}}{I_{STDT1} \epsilon_{STD}}$$

$$C = \frac{I_{T2}}{I_{STDT2} \epsilon_{STD}}$$

$$r(B, C) = \frac{\sum_{q=1}^{Q} |B_q - \bar{B}| \cdot |C_q - \bar{C}|}{Q \cdot S_B \cdot S_C}$$

where: $I_{T1}$=intensity of radiation from the second pixels at the first temperature
$I_{T2}$=intensity of radiation from the second pixels at the second temperature
$I_{STDT1}$=intensity of radiation rom the further pixels at the first temperature
$I_{STDT2}$=intensity of radiation from the further pixels at the second temperature
$\epsilon_{STD}$=the known radiation emissivity
Q=the number of the at least several units
q=is successively each of 1, 2 ... Q
$\bar{B}$=average value of B for the Q units
$\bar{C}$=average value of C for the Q units
$S_B$=standard deviation of B for the Q units
$S_C$=standard deviation of C for the Q units.

9. The method of claim 8 wherein the steps of claim 5 are performed on the first pixels of a monitored unit and on the standard pixel of the monitored unit, the computer deriving the indication of the temperature of the first pixels in response to $$r_{tested}(B, C) = \frac{|B_{test} - \bar{B}| \cdot |C_{test} - \bar{C}|}{S_B \cdot S_C}$$

where $$B_{test} = \frac{I_{T1(test)}}{I_{STDT1(test)} \epsilon_{STD}}$$

$$C_{test} = \frac{I_{T2(test)}}{I_{STDT2(test)} \epsilon_{STD}}$$

$I_{T1(test)}$=intensity of radiation from the first pixels of the monitored unit at the first temperature
$I_{T2(test)}$=intensity of radiation from the first pixels of the monitored unit at the second temperature
$I_{STDT1(test)}$=intensity of radiation from the standard pixel of the monitored unit at the first temperature
$I_{STDT2(test)}$=intensity of radiation from the standard pixel of the monitored unit at the second temperature.

10. The method of claim 7 wherein the computer derives indications of (a) the standard temperature for the first pixels in response to B·r(B,C) and (b) the monitored temperature for the first pixels in response to $B_{test} \cdot r_{tested}(B,C)$, and (c) the deviations between the indications of standard temperature for the first pixels and the monitored temperatures for the first pixels of the monitored 11. The method of claim 7 wherein the computer derives the data representing the standard temperatures for the first pixels by (a) determining first and second measures of the average infrared intensity from the second pixels of the O units at said first and second temperatures, (b) determining a third measure of the deviations of the infrared intensity from the second pixels of each of the O units at the first temperature from the first measure, (c) determining a fourth measure of the deviations of the infrared intensity from the second pixels of each of the O units at the second temperature from the second measure, (d) non-linearly combining the third and fourth measures for each of the O units to derive a first resultant, (e) linearly combining the first resultant, (f) determining first and second indications of the spread of values of the detected intensities from the first pixels at the first and second temperatures, respectively, and (g) combining the second resultant with the first and second indication of the spread of values.

12. The method of claim 7 wherein the computer obtains the standard temperature data for the first pixels from a statistical function of (a) the known emissivity and (b) the detected intensities at the further pixels and at the second pixels of the O units while the O units are at the first and second temperatures.

13. The method of claim 12 wherein the computer combines a value derived from the statistical function with a measure of the detected intensity for the first pixel to provide the indication of the standard temperature for the first pixels.

14. The method of claim 13 wherein the computer derives the statistical function value by determining the average values and the standard deviations of the intensities from the second pixels of the O units at the first and second temperatures, and combining the determined average values and standard deviations.

15. The method of claim 6 wherein the unit includes plural components and the method is performed to detect the expected lifetime of the unit, each of the components occupying a plurality of said first pixels and having known pixel locations on the unit, further comprising using the camera to monitor the intensity of infrared radiation emitted from the first pixels forming the components while the components are stimulated to a higher temperature than ambient temperature of the unit, the computer responding to the radiation indications for the first pixels of each particular component and an indication of the particular component radiation emissivity to derive an indication of expected operating temperature of each particular component, responding to the indication of expected operating temperature of each particular component and a stored value relating expected operating temperature of each particular component to the lifetime of the particular component to derive a second indication representing the expected lifetime of each particular component, and combining the second indications for all of the components to derive the indication of the unit expected lifetime, the temperature indication of each particular component being derived by combining the indications of (a) the monitored radiation intensity from all of the first pixels occupied by the particular component and (b) the radiation emissivity of the first pixels occupied by the particular component.

16. The method of claim 5 wherein the unit includes plural components and the method is performed to detect the expected lifetime of the unit, each of the components occupying a plurality of said pixels and having known pixel locations on the unit, further comprising using the camera to monitor the intensity of infrared radiation emitted from the pixels forming the components while the components are stimulated to a higher temperature than ambient temperature of the unit, the computer responding to the radiation indications for the pixels of each particular component and an indication of the particular component radiation emissivity to derive an indication of expected operating temperature of each particular component, responding to the indication of expected operating temperature of each particular component and a stored value relating expected operating temperature of each particular component to the lifetime of the particular component to derive a second indication representing the expected lifetime of each particular component, and combining the second indications for all of the components to derive the indication of the unit expected lifetime, the temperature indication of each particular component being derived by combining the indications of (a) the monitored radiation intensity from all of the pixels occupied by the particular component and (b) the radiation emissivity of the pixels occupied by the particular component.

17. The method of claim 16 wherein the intensity of the infrared radiation for the pixels is monitored while the unit is at first and second displaced temperatures, and further including monitoring the intensity of infrared radiation emitted from a standard pixel of the unit while the unit is at the first and second temperatures, the standard pixel having known radiation emissivity, and combining indications of the monitored intensity of the infrared radiation of the pixels and the standard pixel while the unit is at the first and second temperatures with an indication of the emissivity of the standard pixel to provide an indication of the temperature of each pixel.

18. The method of claim 5 wherein the indicated property is an indication of worthiness of the unit for its intended use.

19. The method of claim 5 wherein the camera monitors the emission at plural times while the unit is being transiently stimulated.

* * * * *